(12) United States Patent
Kantrowitz

(10) Patent No.: US 7,976,452 B2
(45) Date of Patent: Jul. 12, 2011

(54) LONG TERM AMBULATORY INTRO-AORTIC BALLOON PUMP WITH PERCUTANEOUS ACCESS DEVICE

(75) Inventor: Allen B. Kantrowitz, Williamstown, MA (US)

(73) Assignee: L.Vad Technology, Inc., Detroit, MI (US)

( * ) Notice: Subject to any disclaimer, the term of this patent is extended or adjusted under 35 U.S.C. 154(b) by 543 days.

(21) Appl. No.: 12/154,091

(22) Filed: May 20, 2008

(65) Prior Publication Data
US 2008/0281147 A1 Nov. 13, 2008

Related U.S. Application Data

(63) Continuation-in-part of application No. 10/865,965, filed on Jun. 11, 2004, now Pat. No. 7,374,531, which is a continuation-in-part of application No. 10/746,543, filed on Dec. 24, 2003, now Pat. No. 7,468,050, application No. 12/154,091, which is a continuation-in-part of application No. 11/460,339, filed on Jul. 27, 2006, now Pat. No. 7,704,225.

(60) Provisional application No. 60/477,704, filed on Jun. 11, 2003, provisional application No. 60/703,611, filed on Jul. 29, 2005.

(51) Int. Cl.
*A61N 1/362* (2006.01)
(52) U.S. Cl. .......................................................... 600/18
(58) Field of Classification Search ..................... 600/18
See application file for complete search history.

(56) References Cited

U.S. PATENT DOCUMENTS

| | | | |
|---|---|---|---|
| 3,504,662 A * | 4/1970 | Jones ............................... | 600/18 |
| 3,663,965 A | 5/1972 | Lee, Jr. et al. | |
| 3,720,199 A * | 3/1973 | Rishton et al. ................... | 600/18 |
| 3,906,549 A | 9/1975 | Bucalo | |
| 3,964,470 A | 6/1976 | Trombley | |
| 3,995,644 A | 12/1976 | Parsons | |
| 4,004,298 A | 1/1977 | Freed | |
| 4,015,590 A | 4/1977 | Normann | |
| 4,051,840 A | 10/1977 | Kantrowitz et al. | |
| 4,092,742 A | 6/1978 | Kantrowitz et al. | |
| 4,183,357 A | 1/1980 | Bentley et al. | |
| 4,245,622 A | 1/1981 | Hutchins, IV | |
| 4,321,914 A | 3/1982 | Begovac et al. | |
| 4,407,271 A | 10/1983 | Schiff | |
| 4,522,195 A | 6/1985 | Schiff | |
| 4,576,606 A | 3/1986 | Pol et al. | |
| 4,630,597 A | 12/1986 | Kantrowitz et al. | |
| 4,634,422 A | 1/1987 | Kantrowitz et al. | |
| 4,668,222 A | 5/1987 | Poirier | |
| 4,676,802 A | 6/1987 | Tofield et al. | |
| 4,692,148 A | 9/1987 | Kantrowitz et al. | |
| 4,897,081 A | 1/1990 | Poirier et al. | |

(Continued)

*Primary Examiner* — George Manuel
(74) *Attorney, Agent, or Firm* — Young Basile

(57) ABSTRACT

Disclosed herein are embodiments of long-term ambulatory intra-aortic balloon pump systems for providing left ventricular cardiac assistance to a patient. The systems can comprise an external drive system for supplying a compressed fluid, the drive system operating in accordance with a control program stored in memory, an intra-luminal balloon pump having an elongate inflatable chamber positionable to be lying completely within a descending aorta of the patient, and a percutaneous access device. The percutaneous access device can be a biocompatible implantable portal comprising a communicative passage through an interior bore and an exterior having a neck region adapted to promote autologous cell growth thereon in an implantable region, the neck region having a plurality of channels extending about the neck region.

27 Claims, 11 Drawing Sheets

U.S. PATENT DOCUMENTS

| | | |
|---|---|---|
| 4,976,729 A | 12/1990 | Holfert et al. |
| 5,242,415 A | 9/1993 | Kantrowitz et al. |
| 5,271,746 A | 12/1993 | Pol et al. |
| 5,833,619 A | 11/1998 | Freed et al. |
| 5,833,655 A | 11/1998 | Freed et al. |
| 5,904,666 A | 5/1999 | DeDecker et al. |
| 6,030,335 A | 2/2000 | Franchi |
| 6,031,148 A | 2/2000 | Hayes et al. |
| 6,132,363 A | 10/2000 | Freed et al. |
| 6,471,633 B1 | 10/2002 | Freed |
| 6,503,228 B1 | 1/2003 | Li et al. |
| 2003/0224032 A1 | 12/2003 | Read et al. |
| 2004/0170663 A1 | 9/2004 | Wang |
| 2005/0080338 A1 | 4/2005 | Sirimanne et al. |
| 2005/0181011 A1 | 8/2005 | Hunter |
| 2007/0026032 A1 | 2/2007 | Kantrowitz |

* cited by examiner

LONG TERM AMBULATORY INTRO-AORTIC BALLOON PUMP WITH PERCUTANEOUS ACCESS DEVICE

CROSS-REFERENCE TO RELATED APPLICATIONS

This application is a continuation-in-part of U.S. patent application Ser. No. 10/865,965 filed Jun. 11, 2004, which is a continuation-in-part of U.S. patent application Ser. No. 10/746,543 filed Dec. 24, 2003, which claims the benefit of U.S. provisional patent application Ser. No. 60/477,704 filed Jun. 11, 2003, and this application is a continuation-in part of U.S. patent application Ser. No. 11/460,339 filed Jul. 27, 2006, which claims the benefit of U.S. provisional patent application Ser. No. 60/703,611 filed on Jul. 29, 2005, all of which are incorporated by reference herein in their entirety.

FIELD OF THE INVENTION

The present invention relates to an intra-aortic balloon pump insertable through a vessel entry of the patient, and more particularly to an intra-aortic balloon pump for long term ambulatory use powered through a percutaneous access device.

BACKGROUND OF THE INVENTION

An aortic blood pump can be permanently surgically implanted in the wall of the aorta to augment the pumping action of the heart. The aortic blood pump is sometimes referred to as a mechanical auxiliary ventricle assist device, dynamic aortic patch, or permanent balloon pump. Alternatively, the aortic blood pump can be inserted using minimally invasive technique, and is sometimes referred to as a temporary balloon pump, or simply as a balloon pump, since extended periods of use are possible depending on the method and location of surgical insertion.

Typically, the aortic blood pump includes a flexible bladder to be inflated and deflated in a predetermined synchronous pattern with respect to the diastole and systole of the patient to elevate aortic blood pressure immediately after aortic valve closure. Inflation and deflation of the bladder can be accomplished by means of a supply tube connected to the bladder and can be connected to a percutaneous access device (PAD). The PAD can be permanently surgically implanted in a patient's body to provide a through-the-skin coupling for connecting the supply tube to an extra-corporeal energizing source. Electrical signal leads from electrodes implanted in the myocardium are likewise brought out through the skin by means of the PAD. The "R" wave of the electrocardiograph and/or feature related to the aortic pressure wave form can be employed to control the fluid pressure source to inflate and deflate the inflatable chamber in a predetermined synchronous relationship with the heart action.

The aortic blood pump acts to assist or augment the function of the left ventricle and is typically restricted to use in patients who have some functioning myocardium. The aortic blood pump does not need to be operated full-time, and in fact, can be operated periodically on a scheduled on-time, off-time regimen. Typically, the patient can be at least temporarily independent of the device for periods of one to four hours or more, since the aortic blood pump does not require continuous operation.

Temporary intra-aortic balloon pumps are generally known for insertion through the femoral artery of the leg for emergency patient treatment. Temporary use of the pump was originally intended to last for only a few hours up to a few days for non-ambulatory patients in emergency situations. The temporary intra-aortic balloon pump is limited in size to prevent fully occluding the lumin of the aorta and/or any branch arteries, so that pressures within each location are free to equalize at all times during the pump inflation cycle, and in order to pass percutaneously via an introduction sheath through the smaller diameter of the femoral artery during insertion. Non-ambulatory patients restricted to bed can subsist with the level of cardiac assistance available from the relatively small (e.g. typically 30 to 40 cubic centimeters (cc)) volume of the temporary intra-aortic balloon pump. However, this relatively limited level of cardiac assistance is insufficient, and the typical location of insertion is undesirable, for ambulatory patients. In addition, the temporary intra-aortic balloon pump is typically tightly furled and wrapped in order to allow for insertion through a narrow introduction sheath. The furling and wrapping of the material raises the concern of damage to the material of the balloon pump, which might lead to premature failure when subjected to numerous pumping cycles, if prolonged use over a period greater than a few days is mandated for a particular patient. Further, the power supply conduit to the pump is of limited cross sectional area because of the use of a helium pumping medium in order to provide the desired level of responsiveness to correctly time the inflation and deflation of the temporary intra-aortic balloon pump with respect to the heart beat of the patient. The use of a helium pumping medium may not be as practical as the use of an air pumping medium in order to provide a simple cardiac assistance device for long term ambulatory patients.

In the original description of clinical use of the temporary IABP, the procedure described the open exposure of the femoral artery with end-to-side anastomosis of a short vascular graft. The graft was used as the vascular entry point. As the use of the temporary IABP grew internationally, many variants of this original concept were introduced to solve specific clinical dilemmas. These variants were introduced to permit use of the temporary IABP in patients with unusually small or stenotic femoral vessels, or in patients whose aorta was easily available during thoracotomy or in patients needing the temporary IABP as a bridge-to-transplant. Distal ischemic complications are a concern in many of these methods. Techniques that use an end-to-side vascular graft may be less prone to this complication. Variant vascular entry points that have been described for the temporary IABP have included: (1) open approach to the femoral artery with cannulation via an end-to-side vascular grafts; (2) percutaneous approach to the femoral artery; (3) open approach to the iliac artery; (4) retro peritoneal approach; (5) during open thoracotomy for a standard open-heart procedures, the open trans thoracic approach with direct cannulation with the aorta; (6) during open thoracotomy for standard open-heart procedures, the open trans thoracic approach with cannulation via end-to-side vascular graft; (7) large aortic caliber side graft for cul-de-sac placement; and (8) axillary artery approach with cannulation either directly or via an end-to-side vascular graft.

To alleviate some of the limitations and difficulties associated with the catheter-based temporary intra-aortic balloon pump, a permanent balloon pump in the form of an elliptical patch supporting the pumping chamber was disclosed in U.S. Pat. No. 4,630,597 for incorporation into the wall of the aorta by a surgeon. Permanent use of the pump was intended to last for a prolonged period of time extending from a few months up to several years for ambulatory patients who required cardiac assistance for extended periods of time. The procedure required the surgeon to perform a left thoracotomy, cross clamp the aorta, and then fashion a suture line around the perimeter of the patch. An advantage of this configuration was that the geometry of the thoracic aorta is expanded, allowing the displacement volume of the pumping chamber to be in the desired range of 60 cubic centimeters (cc) to 65 cubic centimeters (cc), inclusive, thereby enhancing the clinical effectiveness of the CARDIOVAD® device.

U.S. Pat. No. 5,484,385 discloses an intra-aortic balloon catheter. This patent addresses the potential problem of a thin wall balloon failing by rupture believed to be due to abrasion between the thin wall of the balloon and the inner wall surface of the aorta. Typically, a balloon catheter has a thin wall thickness in order to provide for furling the balloon into a small uniform diameter dimension for surgical insertion through the femoral artery to a position below the aortic arch and the left subclavian artery before unfurling. The patent proposes increased wall thickness and reduced outer diameter of the balloon to provide a narrower tapered distal end of the balloon within the narrower portion of the aorta with the narrower portion of the aorta. However, this patent does not recognize or address the potential tortuosity of the aorta that typically can occur in patients, where the aorta is not smooth and uniform in a two-dimensional plane as depicted in medical books, but rather twists and turns through three-dimensional space within the body cavity creating greater difficulty in properly positioning and operating a balloon pump within the descending aorta of the patient.

U.S. Pat. No. 4,527,549 discloses a method of and means for intra-aortic assist. The patent asserts that the position of the balloon is more important than the size of the balloon, and that the proper position for a balloon is at the root of the aorta right above the valve in the ascending portion of the aorta. In order to traverse the aortic arch, the patent proposes preforming the device to follow the aortic arch. While the patent suggests the use of multi-segment balloons, it specifically teaches that the appropriate position for the first balloon is immediately above the valve in the ascending portion of the aorta. This patent does not recognize the difficulty in positioning a balloon within the ascending portion of the aorta and/or the difficulty in passing a preformed portion corresponding to the arch of the ascending aorta through the serpentine tortuous descending portion of the aorta. The patent does not address the potential clinical danger of stroke created by a catheter moving across the entrances to the arch vessels (e.g. the left subclavian artery, the left common carotid artery, and the innominate artery). The clinical danger of stroke, by way of example and not limitation, can be linked to: (1) risk of dislodgment of embolus or plaque into the arch vessels during insertion of the balloon pump around the arch into the ascending aorta; (2) risk of occlusion of the arch vessels; (3) risk of repeated abrading action against the surface of the arch and entrance to the arch vessels; and (4) risk of dislodgment of embolus or plaque during withdrawal or replacement of the balloon pump. In summary, the patent does not recognize that the risks associated with positioning the proximal balloon in the ascending aorta outweigh the benefits achieved, and that a larger size balloon in the descending aorta alleviates the need to entertain the risk of entering the ascending aorta in order to provide the amount of assistance desired for an ambulatory patient.

U.S. Pat. No. 6,468,200, U.S. Pat. No. 3,791,374, and U.S. Pat. No. 3,504,662 each disclose segmented balloon pumps adapted to be actuated at different rates. For example, U.S. Pat. No. 3,504,662 discloses actuation of the middle compartment prior to or at a more rapid rate than the end compartments. U.S. Pat. No. 6,468,200 discloses the chambers are inflated sequentially beginning with the chamber closest to the aortic root, in order to advance the blood in the downstream direction. Each of these patents teaches the desirability of a temporal sequence of inflation and/or deflation, even though such procedures are of undetermined effectiveness and accordingly are not well established as providing the amount of assistance desired for an ambulatory patient.

An article published by The Society of Thoracic Surgeons in 2002 entitled "Ambulatory Intraaortic Balloon Pump Use as Bridge to Heart Transplant" taught the advantage of using a catheter based intraaortic balloon pump positioned in the descending aorta accessed through an expanded polytetrafluoroethylene vascular conduit graft to the left axillary artery. The procedure allowed the patient to be ambulatory, and allowed multiple exchanges of the catheter based intraaortic balloon pump for extended use (12 days to 70 days). The positioning of the intraaortic balloon was similar to the conventional positioning, except the distal end of the balloon was maintained above the renal arteries and the proximal end of the balloon was positioned just below the subclavian artery in the descending aorta. While pointing out the benefits of maintaining ambulatory patients, the article did not reflect the desirability of increased balloon pump volume for ambulatory patients, and/or the desirability of increased conduit diameter for maintaining balloon pump cycle timing for larger volume balloon pumps, and/or the desirability of a percutaneous access device for connecting the catheter based intraaortic balloon pump to the drive system for an ambulatory patient or the difficulties encountered by chronic abrasion between the straight pumping chambers and the inner wall of the aorta.

SUMMARY OF THE INVENTION

Disclosed herein are long-term ambulatory intra-aortic balloon pump systems for providing left ventricular cardiac assistance to a patient. One such system comprises an external drive system for supplying a compressed fluid, the drive system operating in accordance with a control program stored in memory, an intra-luminal balloon pump having an elongate inflatable chamber positionable to be lying completely within a descending aorta of the patient and a percutaneous access device for connecting in fluid communication the intra-luminal balloon pump with the compressed fluid to be supplied by the external drive system. The elongate inflatable chamber is inflated and deflated synchronously with a heartbeat of the patient in accordance with the control program stored in memory of the external drive system.

Another embodiment of a long-term ambulatory intra-aortic balloon pump system for providing left ventricular cardiac assistance to a patient comprises an external drive system for supplying a compressed fluid, the drive system operating in accordance with a control program stored in memory, an intra-luminal balloon pump having an elongate inflatable chamber positionable to be lying in a descending aorta completely downstream of the aortic arch and carotid arteries of the patient and a percutaneous access device for connecting in fluid communication the intra-luminal balloon pump with the compressed fluid to be supplied by the external drive system. The device comprises a wall defining a bore and an exterior having a neck region adapted to promote autologous cell growth thereon in an implantable region. The elongate inflatable chamber is inflated and deflated synchronously with a heartbeat of the patient in accordance with the control program stored in memory of the external drive system. Alternatively, the percutaneous access device for connecting in fluid communication the intra-luminal balloon pump with the compressed fluid to be supplied by the external drive system comprises a wall defining a bore and an exterior having a neck region adapted to promote autologous cell growth thereon in an implantable region, and with a pore size and configuration which avoids regions which are of a geometry to allow bacteria to grow and multiply but which are of the pore size and configuration which would interfere with a body's white cells from reaching the bacteria.

An aortic blood pump can include an elongate semi-rigid shell portion having a concave inner surface and a flexible membrane integrally bonded to the peripheral edge surface of the shell portion to define a chamber between the concave inner surface and the membrane, and at least one anchor member for attaching the blood pump with respect to the wall of the descending aorta. The anchor member can include a stent located at one end of the blood pump, or at both ends of the blood pump, or at each end of each inflatable chamber defining the blood pump, or extending longitudinally to sheath at least one of the inflatable chambers defining the blood pump. The stent can be at least attached to the flexible conduit extending to the at least one inflatable chamber, and/or can be partially embedded in the shell portion to position the shell portion in proximity to the inner wall of the aorta, and/or the stent can completely surround at least one of the inflatable chambers defining the balloon pump.

An aortic blood pump can assist cardiac function during a cardiac cycle of a patient when positioned with respect to an aorta of the patient. The aortic blood pump can include an elongate semi-rigid shell having a contoured, concave inner surface terminating at a peripheral side edge. A flexible membrane can be continuously bonded to the shell adjacent the peripheral side edge to define an enclosed inflatable chamber. At least one passage can extend through the shell into communication with the inflatable chamber to inflate and deflate the chamber. A stent can be partially embedded in the shell and/or can be connected to the outer surface of the semi-rigid shell to extend outwardly from the shell to define a substantially open cylindrical area for expansion of the flexible membrane when inflated. The stent can be movable between an expanded position and a retracted position. The retracted position of the stent can reduce the overall diameter of the device to facilitate minimally invasive surgical implantation. When properly positioned within the aorta, the stent can be expanded to define the substantially open cylindrical area encompassing the zone of inflation of the flexible membrane within the aorta.

An inflatable balloon pump can also be supported by being suspended within a central portion of a collapsed or retracted stent for minimally invasive surgical positioning with respect to the aorta of the patient. After expansion of the stent in an endoscopically selected location of the aorta, the inflatable balloon pump can be cyclically inflated and deflated to assist the cardiac function based on measured clinical parameters of the patient.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1C:
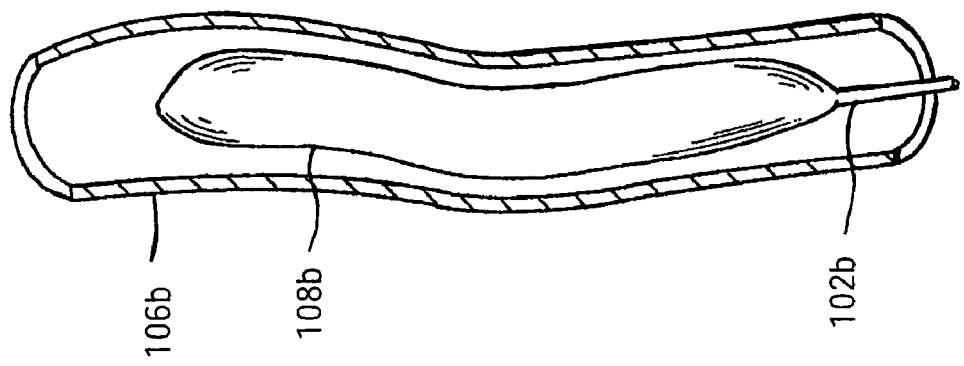
FIG. 1C is a detailed cross-sectional view of the single chamber balloon pump of FIG. 1A in an inflated state after insertion through a lower body skin entry point and/or lower body vascular entry point.

Various embodiments are shown throughout the Figures illustrating the present invention, and include common elements in different structural configurations where common elements are designated with a common base numeral and differentiated with a different alphabetic designation for the various embodiments. Descriptions for the base numeral designations are considered to be generic to the different alphabetic extensions added to the alternative embodiments except as specifically noted herein.

The present invention provides a pumping chamber lying completely within the lumin of the aorta rather than being embedded or implanted in the wall of the aorta. By way of example and not limitation, a surgeon can anastomose a length of vascular graft end-to-side directly to the aorta and use this graft as the aortic cannulation point. The vascular graft can be long enough to reach the subcutaneous skin layer, thereby simplifying exchange of the LTIABP if exchange becomes necessary due to clinical circumstances. It is expected that the placement of the graft and the LTIABP could be performed either with open surgical techniques, percutaneous techniques, or with endoscopic techniques via the thoracic cavity, the retroperitoneal space or the thoracic outlet or other anatomic sites.

According to the present invention, the size of the blood pump 108 and the power/signal conduit 102 can both be made larger than in the case of the temporary IABP. This enlarged configuration allows for various advantages over the temporary IABP. A larger displacement volume for the LTIABP according to the present invention is desired for ambulatory patients compared with the temporary IABP, since ambulatory patients have larger circulatory demand requirements than sedentary patients. The long term ambulatory status of the patient would be best served by the use of air rather than helium as the driving medium, thereby obviating the need for storage and periodic replacement of lost helium in the apparatus. Viscosity differences between air and helium necessitate the use of a larger diameter pneumatic power conduit 102 when air is used in order to preserve the dynamic responsiveness of the cardiac assist device.

First, to provide a larger displacement volume for the LTIABP, the pumping chamber 108a of the LTIABP according to the present invention is longer than that of the temporary IABP giving the LTIABP a larger stroke volume (improving its clinical effectiveness) compared with the temporary IABP. The longer length requires additional modifications, such as a tapered shape in order to minimize risk of injury to the subclavian, carotid, celiac, mesenteric and renal arteries. The longer length raises two concerns: intermittent occlusion of the entrance to major branch arteries and abrasion against the inner wall of the aorta in case of tortuous aorta. A tortuous aorta is a common presentation in many patients with cardiovascular disease sufficiently advanced to warrant consideration of mechanical support of the failing heart. These concerns are met with the design of the LTIABP according to the present invention by tapering the ends of the pumping chamber 108a and/or segmenting the pumping chamber into one or more subsegments 108, 110, 112, 114 each separated by a flexible power conduit 102 link. These links would allow the long axis of each segment of the pumping chamber to align with a local longitudinal axis of a local segment of the surrounding aortic lumin containing the corresponding inflatable chamber. Moreover, the diameter of each segment can be different. Thus, the segmented pumping chamber of the LTIABP according to the present invention, together with the intervening links, can allow the device according to the present invention to accommodate variations in the tortuous or serpentine shape of the aorta and variations in the diameter of the aorta. This type of segmentation of the pumping chamber is distinguishable from mono-chamber temporary IABP devices which can not adapt to a tortuous aorta, and is distinguishable from multi-chamber temporary IABP devices which have been introduced in the past in order to influence the inflation and deflation characteristics, as well as timing and directionality characteristics, of the pumping chambers.

Second, the wall structure of the LTIABP according to the present invention can be more rugged when compared to the conventional temporary IABP, thereby improving the flex life. This permits selection of alternative materials and/or additional thickness of conventional materials, or layering wall structures to improve the flex life of the LTIABP device according to the present invention. The present invention does not require the tight furling necessary for conventional insertion of a temporary IABP device through the femoral artery. It is believed that tight furling may on occasion cause injury to the molecular structure of the conventional temporary IABP pumping membrane.

Third, according to the present invention, the power/signal conduit 102 can be of larger diameter thereby improving the performance characteristics of the system determined by that parameter; improving clinical effectiveness at high heart rates; and improving effectiveness with air (rather than helium) as the driving fluid. Allowing air as the driving fluid, in addition to helium, is an important advantage in long term use, since helium needs to be slowly replenished on an ongoing basis. However, in order to maintain the flow rate of air during use as the driving fluid, a large diameter pneumatic power conduit 102 is required.

The temporary IABP was originally intended as a device for short term (i.e. hours up to days) management of acute heart failure (CHF). Accordingly, the skin entry point was managed clinically as a simple catheter puncture site. After approximately 5-7 days, such skin puncture sites allow colonization of the catheter surface. Straight forward efforts to confine such bacterial colonization of catheter entry sites to the subcutaneous plane with a cuff (such as with the HICKMAN® and GROSHONG® catheters) can extend the useful lifetime of the catheter for weeks and months, but are not robust enough to reliably solve the bacterial contamination problem for months and years. The problem of long term percutaneous access for power and signal conduits was addressed in the percutaneous access device 10 (PAD) designed for use with the CARDIOVAD® permanent blood pump as disclosed in U.S. Pat. No. 5,833,655 which is incorporated by reference herein. An alternate percutaneous device is disclosed in U.S. Pat. No. 5,242,415 which is incorporated by reference herein. Preferably, the percutaneous access device is cultured with cells prior to the implantation by any suitable method, by way of example and not limitation, such as the methods described in U.S. Pat. No. 4,913,700 and U.S. Pat. No. 4,810,246 which are incorporated by reference herein. The percutaneous access device 10 can be adapted to convey the power/signal conduit 102 of the LTIABP according to the present invention. The PAD 10 provides for a stable interface to be established between the skin and the LTIABP device and also provides for a break away point in the conduit to allow the patient to be disconnected from the drive system P as clinical status permits.

As in the existing CARDIOVAD® permanent blood pump device, the present invention can include signal sensors implanted in locations separate from the pumping chamber or integrated into the pumping chamber and yet still be integrated into the percutaneous access device 10 (PAD) in order for the signal sensor leads to be passed through the skin to the LTIABP.

As an alternative to cell culturing on a percutaneous access device, a percutaneous access device surface and process to enhance autologous cell growth into a stable long term relation to the device has been developed. The stabilization of a PAD within the skin to form a germ-free barrier requires subject cells to grow onto the neck surfaces of the PAD adjacent to the subject's epidermis. The present invention uses alone, or in combination cell channeling contours, porous biodegradable polymers and the application of vacuum to promote cellular growth towards the surface the neck of a PAD. The present invention in facilitating rapid cellular colonization of a PAD neck allows the subject to act as their own cell culture facility and as such affords more rapid stabilization of the PAD, and lower incidence of separation and infection.

Figure 21:
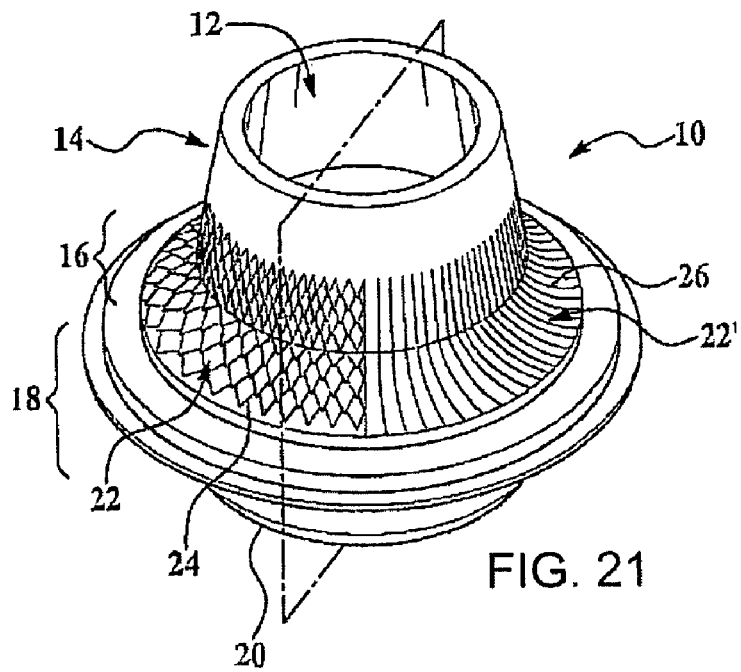
FIG. 21 is a composite perspective view depicting two exemplary cell growth channel pattern halves to an inventive percutaneous access device joined together where the cell growth channels are not depicted to scale for visual clarity.
Figure 22:
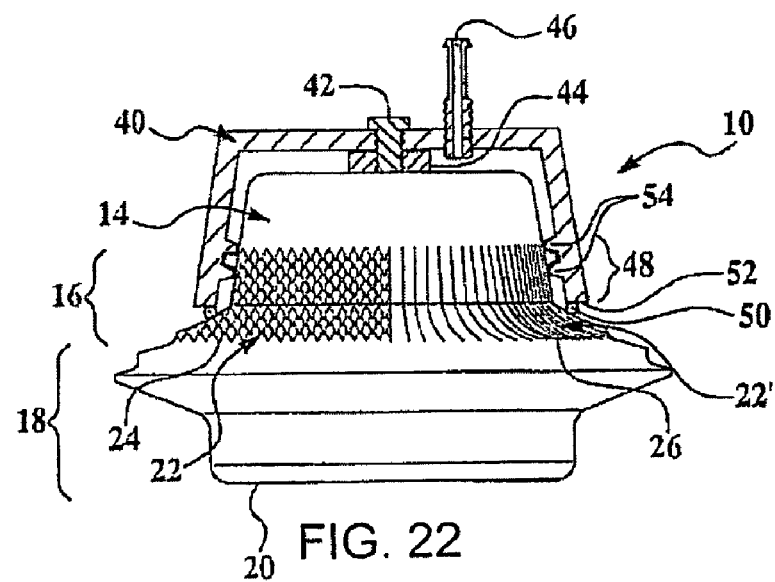
FIG. 22 is a plan view of the percutaneous access device depicted in FIG. 1 with a cross-sectional view along with a cross-sectional view of a vacuum manifold coupled thereto.
Figure 23:
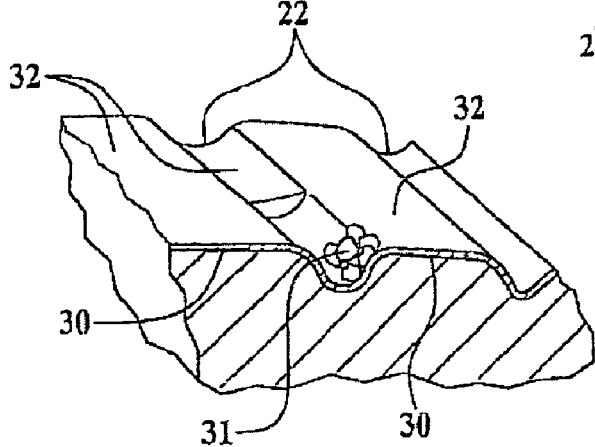
FIG. 23 is a perspective view of a cell growth channel according to the present invention.

Referring now to the FIGS. 21-23, an inventive portal is shown generally at 10. The portal 10 has an opening 12 defined by a sidewall 14, the exterior side of the wall 14 defining a neck region 16 adapted to promote growth of autologous fibroblast cells thereon. A suitable exterior side surface substrate for fibroblast growth is a nanotextured polycarbonate (LEXAN) as detailed as a sleeve in U.S. Pat. No. 4,634,422. Unfortunately, the process of fission product bombardment followed by etching in a base solution detailed yields a range of pits and pores that vary in size to an extent that some of the pores are large enough to harbor pools of extracellular fluid and bacteria. A preferred method of generating a nanotextured neck surface yields pore sizes that are uniformly less than 500 to provide an anchor point for a fibroblast podocyte, while having dimensions that disfavor bacterial colonization. More preferably, a nanotextured surface as used herein has a uniform distribution of 50 to 500 nanometer median dimension indentations. Most preferably, the indentations have a median dimension of between 100 and 300 nanometers. Beneath the neck region 16 lies an implanted region 18 terminating in an inward portal face 20, that is communicative with the opening 12 to form a passage through which fluids, electrical signals, gases or a combination thereof are communicated. The neck region 16 has a pattern of contoured autologous cell-conveying channels 22 or 22'.

It is appreciated that the channels can take a variety of forms. The channel 22 is formed by methods such as imprinting, embossing, molding or machining into the portal 10. A channel 22 can have dimensions on the order of two to ten times the diameter of a plasma-borne fibroblast that is equivalent to 20 to 300 microns since a fibroblast has a diameter from 10 to 15 microns. More specifically, a channel 22 has a width of between 30 and 120 microns. Most specifically, channel 22 is devoid of discontinuities and acute angles that disfavor cellular planarization and adhesion. A parabolic cross section is exemplary of a channel facilitating fibroblast growth. Typically, the plateau region between adjacent channels 22 has a width ranging from 0 to 600 microns. Preferably, the transition between the channel 22 and the plateau 30 is devoid of discontinuities and acute angles that disfavor cellular planarization and adhesion. A non-existent zero micron width plateau 30 corresponds to the instance where the cross section between channels corresponds to a sinusoidal pattern or the edges of adjacent parabolic channels intersect. Preferably, a plateau 30 has a width relative to an adjacent channel width that defines a ratio between 0.5 and 3:1. The alternation of channels 22 and plateaus 30 according to the present invention facilitates capillary draw of fibroblasts up into the neck region 16 of the inventive device 10.

Optionally, the neck region 16 is coated with a substance to facilitate cellular infiltration and growth on the neck region 16. Such coating substances include cell growth scaffolding matrices as detailed in U.S. Pat. Nos. 5,874,500; 6,056,970; and 6,656,496; and Norman et al. Tissue Eng. 3/2005, 11(3-4) pp. 375-386. Preferably, autologous plasma from the subject receiving an inventive portal 10 is applied to the neck region 16 as part of a scaffold matrix or independent thereof. More preferably, the coating 32 is porous in order to enhance capillary draw. More preferably, the coating 32 is porous and biodegradable. The coating has pores typically of an average size of between 10 and 500 microns, and preferably, of an average size of between 30 and 50 microns.

In summary, the LTIABP according to the present invention merges the simplified surgical implantation procedure of the catheter-based conventional temporary IABP with the advantages of the CARDIOVAD® permanent blood pump. The long term intra-aortic balloon pump according to the present invention uses an enlarged balloon pump with less severe folding and wrapping when compared with the conventional temporary IABP. If desired, ECG electrodes can be integrated into the balloon pump as is conventional, and can include at least one electrode, and preferably two or more electrodes. The power conduit delivering compressed fluid to the balloon pump can include an additional channel, possibly centrally located, allowing access for a guide wire, or placement of a pressure sensor, or for blood sample monitoring. The pressure sensor can take any suitable form from commercially available products, such as a conventional electrical strain gauge transducer or an optical based pressure transducer. If an alternative or supplement to a conventional pressure sensor is desired, the present invention can be used with a partial inflation and/or deflation cycle for blood pressure measurement as described in more detail in U.S. Pat. No. 5,833,619, U.S. Pat. No. 5,904,666, U.S. Pat. No. 6,042,532, U.S. Pat. No. 6,132,363, and/or U.S. Pat. No. 6,511,412, all of which are incorporated by reference herein in their entireties.

Figure 1B:
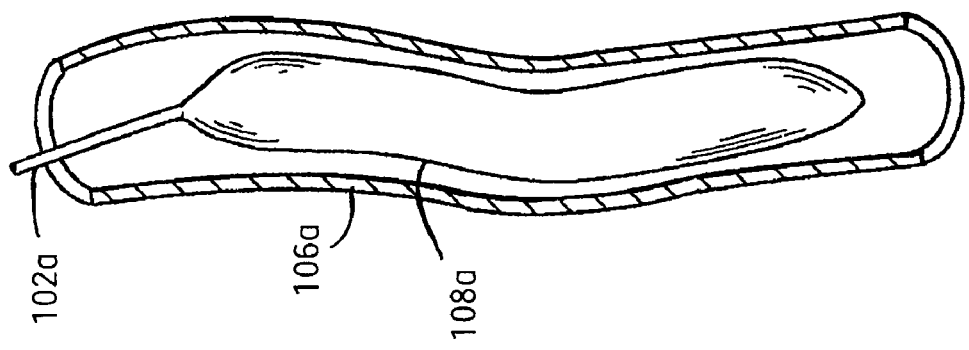
FIG. 1B is a detailed cross-sectional view of the single chamber balloon pump of FIG. 1A in an inflated state.
Figure 1A:
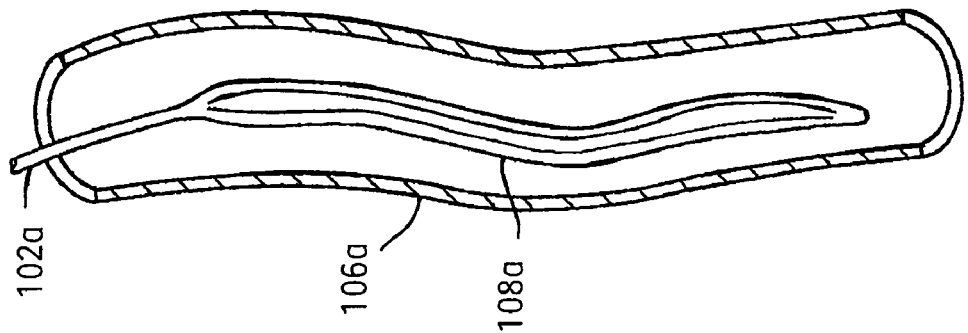
FIG. 1A is a detailed cross-sectional view of a vascular entry into the aorta illustrating a single chamber, large volume, long term intra-aortic balloon pump according to the present invention in a deflated state after insertion through an upper body skin entry point and/or upper body vascular entry point.
Figure 2C:
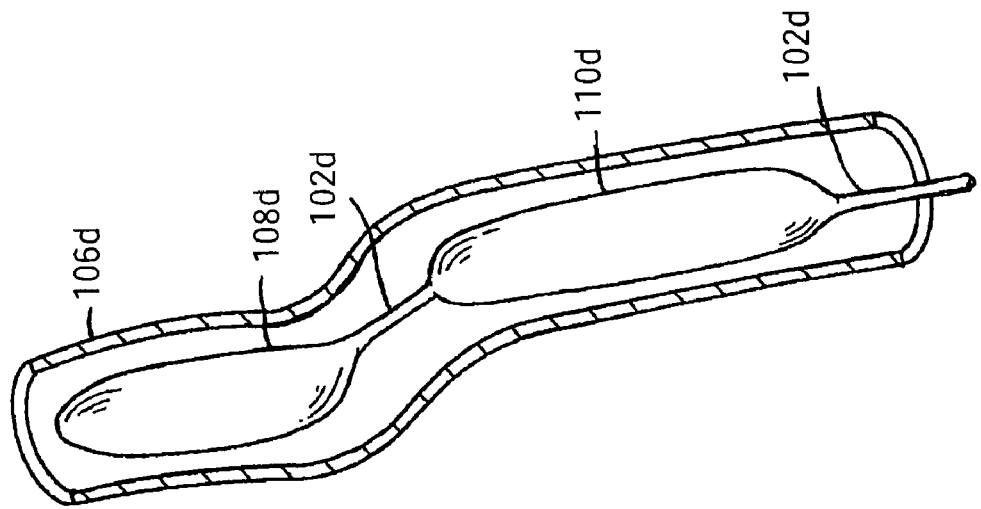
FIG. 2C is a detailed cross-sectional view of the double chamber balloon pump of FIG. 2A in an inflated state after insertion through a lower body skin entry point and/or lower body vascular entry point.
Figure 2B:
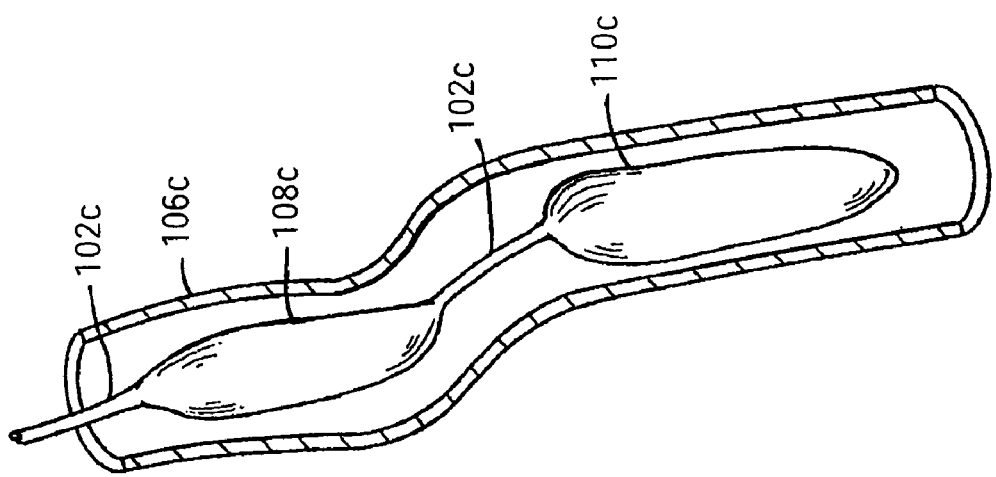
FIG. 2B is a detailed cross-sectional view of the double chamber balloon pump of FIG. 2A in an inflated state.
Figure 2A:
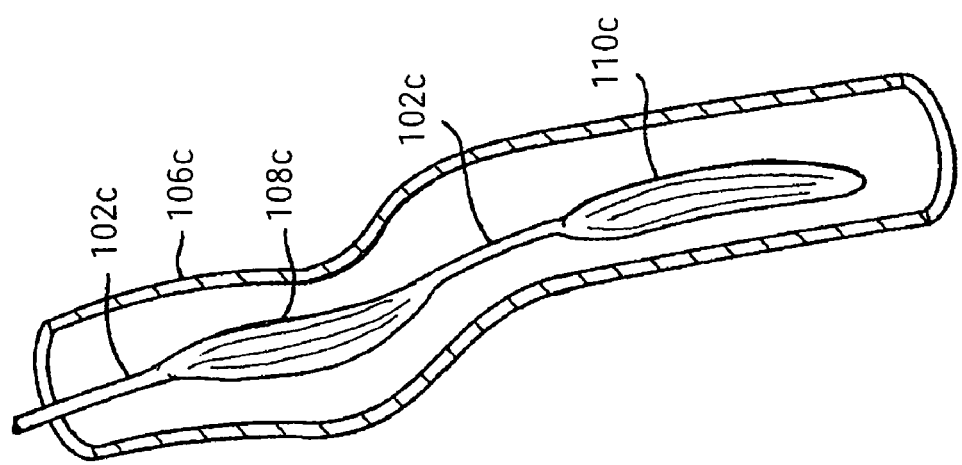
FIG. 2A is a detailed cross-sectional view of a vascular entry into the aorta illustrating a double chamber, large volume, long term intra-aortic balloon pump according to the present invention in a deflated state after insertion through an upper body skin entry point and/or upper body vascular entry point.
Figure 3C:
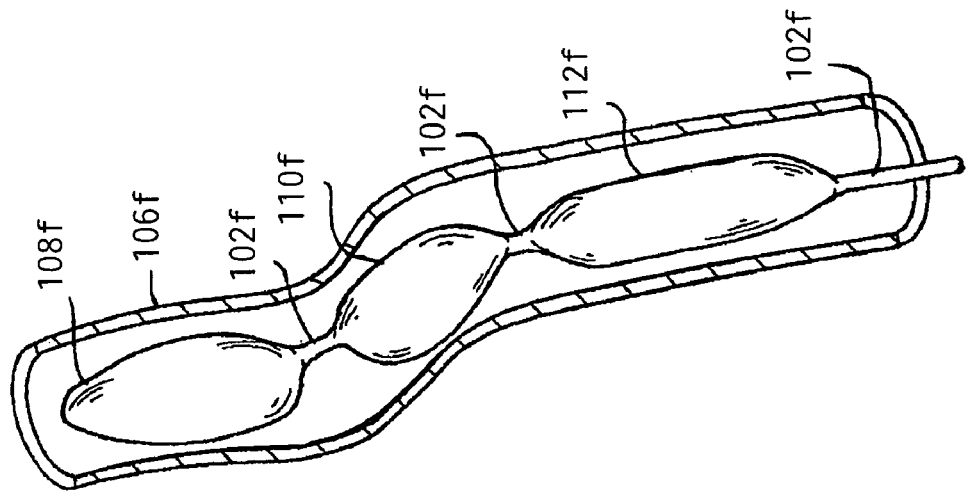
FIG. 3C is a detailed cross-sectional view of the triple chamber balloon pump of FIG. 2A in an inflated state after insertion through a lower body skin entry point and/or lower body vascular entry point.
Figure 3B:
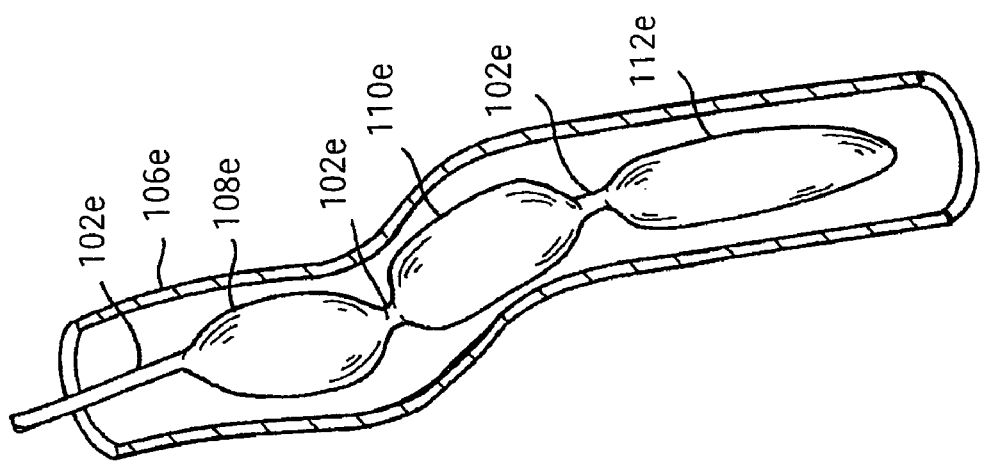
FIG. 3B is a detailed cross-sectional view of the triple chamber balloon pump of FIG. 2A in an inflated state.
Figure 3A:
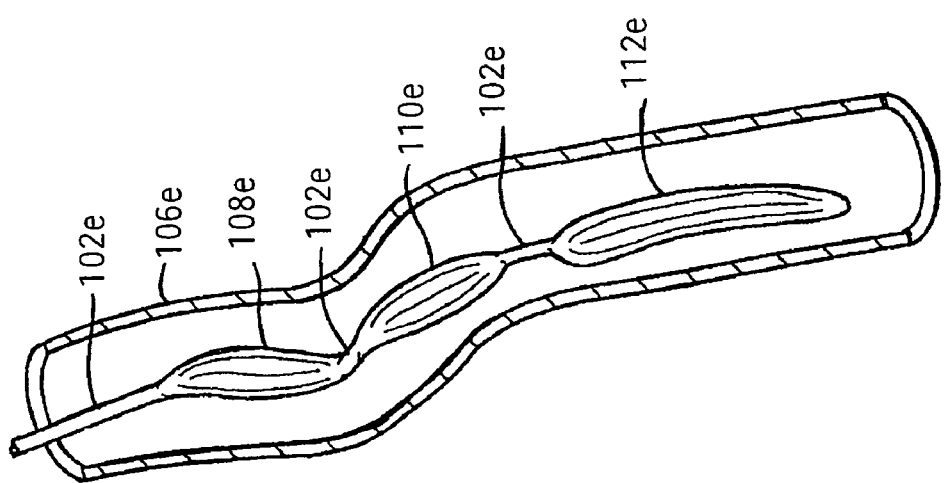
FIG. 3A is a detailed cross-sectional of a vascular entry into the aorta illustrating a triple chamber, large volume, long term intra-aortic balloon pump according to the present invention in a deflated state after insertion through an upper body skin entry point and/or upper body vascular entry point.
Figure 4C:
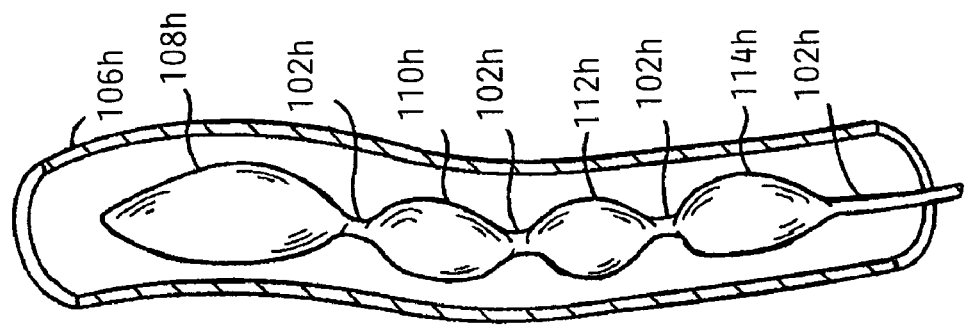
FIG. 4C is a detailed cross-sectional view of the quadruple chamber balloon pump of FIG. 2A in an inflated state after insertion through a lower body skin entry point and/or lower body vascular entry point.
Figure 4B:
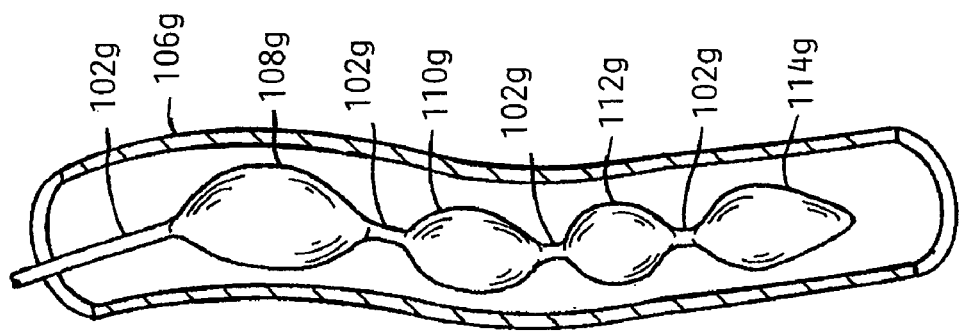
FIG. 4B is a detailed cross-sectional view of the quadruple chamber balloon pump of FIG. 2A in an inflated state.
Figure 4A:
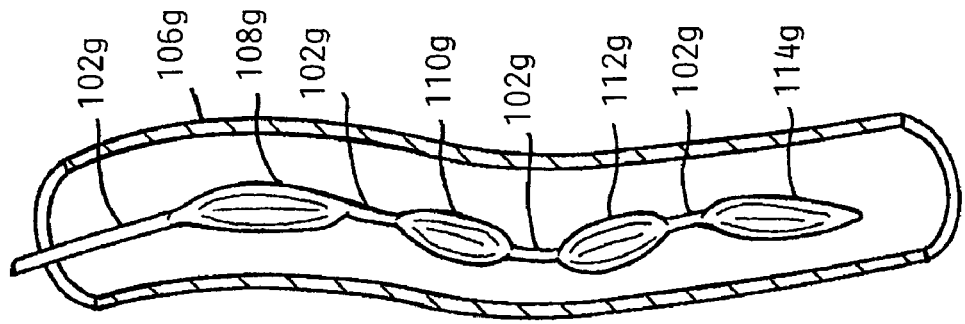
FIG. 4A is a detailed cross-section of a vascular entry into the aorta illustrating a quadruple chamber, large volume, long term intra-aortic balloon pump according to the present invention in a deflated state after insertion through an upper body skin entry point and/or upper body vascular entry point.

The long term intra-aortic balloon pump according to the present invention is intended for long term use. The phrase "long term" as used in conjunction with the LTIABP of the present invention refers to the ability of the LTIABP to be used by ambulatory patients for extended or prolonged periods of time, on the order of several months up to several years, compared with the relatively limited period of time, on the order of hours up to several days or weeks, capable of being used by sedentary patients on a single conventional temporary IABP. The long term intra-aortic balloon pump according to the present invention has increased inflated volume on the order of 50 cc to 65 cc, inclusive, which is comparable to the CARDIOVAD® permanent blood pump, rather than the 35 cc to 40 cc inflated volume provided by the conventional temporary IABP. To provide the desired inflated volume, the LTIABP according to the present invention is elongated along the longitudinal axis. The pumping chamber 108a, 108b of the LTIABP has tapered outer ends as illustrated in FIGS. 1A-1C and/or is segmented into one or more subsegments 108c-108h, 110c-110h, 112e-112h, 114g-114h, each subsegment separated by a flexible power conduit length 102c-102h as illustrated in FIGS. 2A-2C, 3A-3C, and 4A-4C. According to the present invention, the LTIABP is an intra-luminal balloon, and there is no increase in aorta cross section, as is the case with the CARDIOVAD® permanent blood pump. Since the LTIABP according to the present invention is longer, the pump chamber can straddle the diaphragm of the patient. In the segmented pumping chamber configuration according to the present invention, the chambers can have independent diameters with respect to one another, where the diameters decrease in diameter further along the aorta from the heart. This implies a configuration capable of being inserted from below the diaphragm upwardly within the aorta, and alternatively, another configuration capable of being inserted from an upper body point of entry downwardly within the aorta as illustrated in FIGS. 1A-1B, 2A-2B, 3A-3B, and 4a-4b. It should also be recognized that the present invention can be scaled down in size for special clinical circumstances, for example to accommodate a petite patient.

The LTIABP according to the present invention can be used with any skin access connector. By way of example and not limitation, the LTIABP according to the present invention can be used in combination with the percutaneous access device of the present invention as disclosed in U.S. Pat. No. 5,833,655, the specification of which is incorporated by reference herein. The PAD can be sized and shaped for surgical implantation in any desired location of the patient's body suitable for the particular skin entry point of the LTIABP. Furthermore, the PAD according to the present invention can be used with any balloon pump. By way of example and not limitation, the PAD according to the present invention can be used with a conventional temporary IABP to allow small vessel surgical entry while providing long term connection through the skin.

Suitable techniques for implantation of PAD 10 are known to the skilled artisan and include but are not limited to the method described in U.S. Pat. No. 4,634,422, the specification of which is incorporated by reference herein. The general type of PAD can be employed, for example, to supply a pneumatic connection and electrocardiogram lead connections to a dynamic aortic patch of the type disclosed in Kantrowitz et al, U.S. Pat. No. 4,051,840, the specification of which is incorporated by reference therein.

Figure 5:
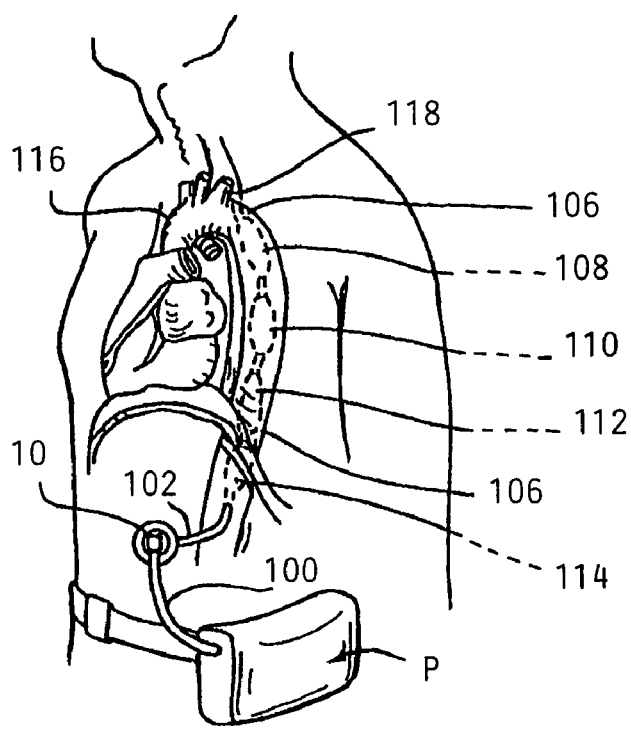
FIG. 5 is a schematic diagram illustrating the PAD device used in combination with an internally implanted balloon pump and an external monitoring/control pump device.
Figure 6:
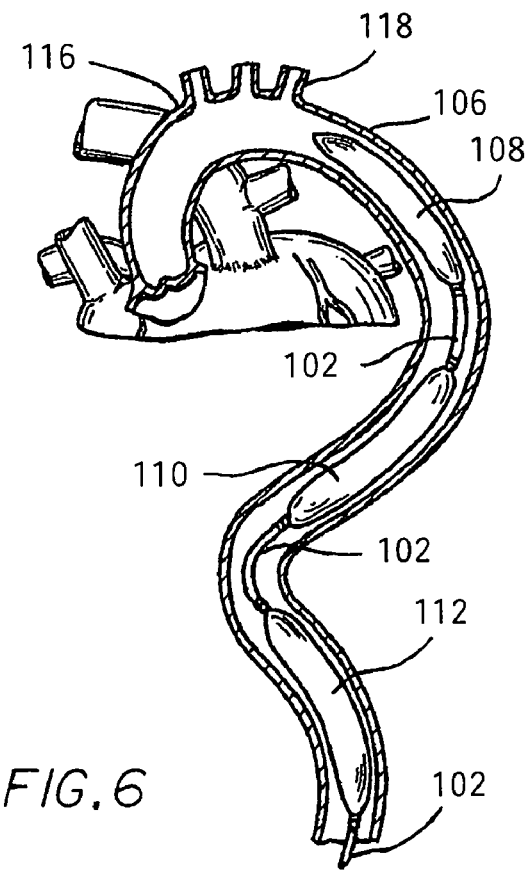
FIG. 6 is a partial view of a human heart and associated arteries showing in cross-section the position of a balloon pump according to the present invention within the descending aorta while depicting a three-dimensional serpentine tortuous descending aorta which has been exaggerated for purposes of illustration in the two-dimensional drawing.

Referring now to FIGS. 5 and 6, a catheter 102 attachable to a pump P is inserted into a descending aorta 106 within the body of a patient. The catheter is of relatively large diameter and is attached to a series of balloons 108, 110, 112, 114 which are pushed from an artery into the descending aorta 106 with the uppermost balloon 108 positioned in the descending aorta 106 below the aortic arch 116 and more particularly, downstream of the arch arteries 118. A plurality of balloons 108, 110, 112, 114 are spaced longitudinally from one another along the catheter 102 providing a total inflatable volume between 50 cc to 65 cc, and more particularly between 55 cc to 65 cc, and most particularly between 60 cc to 65 cc inclusive.

The external pump system P can supply a pressurized fluid, such as compressed air, while being operated according to a control program stored in memory in order to provide cardiac assistance to a patient. Additional details regarding suitable control programs and methods of operation adaptable for use with the present invention can be obtained from U.S. Pat. No. 6,511,412 issued Jan. 28, 2003; U.S. Pat. No. 6,471,633 issued Oct. 29, 2002; U.S. Pat. No. 6,132,363 issued Oct. 12, 2000; U.S. Pat. No. 6,042,532 issued Mar. 28, 2000; U.S. Pat. No. 5,904,666 issued May 18, 1999; U.S. Pat. No. 5,833,655 issued Nov. 11, 1998; U.S. Pat. No. 5,833,619 issued Nov. 10, 1998; U.S. Pat. No. 5,242,415 issued Sep. 7, 1993; U.S. Pat. No. 4,634,422 issued Jan. 6, 1987; and U.S. Pat. No. 4,630,597 issued Dec. 23, 1986 which are incorporated by reference in their entirety herein.

Figure 7:
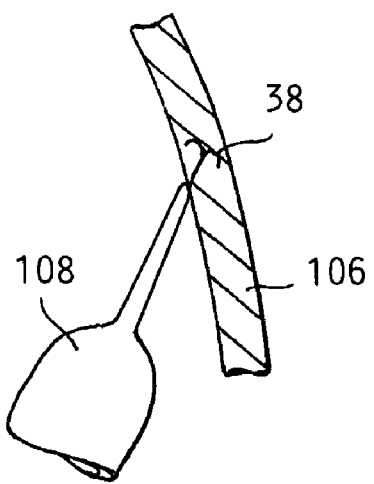
FIG. 7 is a simplified schematic view of at least one anchor member including a hook or barb according to the present invention for anchoring the aortic blood pump in a desired location with respect to the descending aorta of a patient.

Referring now to FIG. 7, the at least one anchor member 38 according to the present invention can include a distal tip of the pump 108 carrying at least one barb or hook capable of being driven into a position partially embedded within the thickness of a wall of the descending aorta 106. If desired, the anchor member 38 can be located at both ends of the pump to tether the pump in a desired location at both ends along the descending aorta 106. It should be recognized that a plurality of barbs can be provided as anchor members 38 in various locations along the longitudinal length of the pump. By way of example and not limitation, the barbs can be located at each longitudinal end of each inflatable chamber dividing the pump, if desired.

Figure 8:
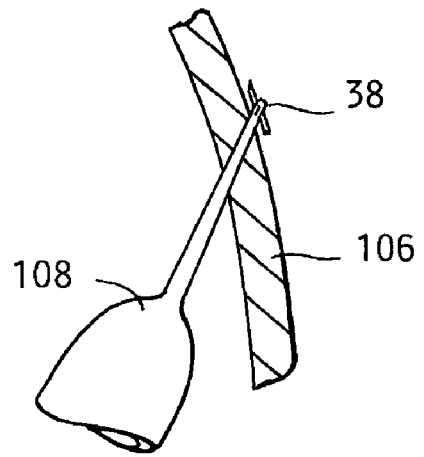
FIG. 8 is a simplified schematic view of at least one anchor member including a suture needle for attachment of an aortic balloon pump according to the present invention to a wall of a descending aorta of a patient.

Referring now to FIG. 8, the at least one anchor member 38 according to the present invention can include a distal tip of the pump 108 carrying at least one needle, sheathed or unsheathed, with integral sutures capable of being driven through a full thickness of a wall of the descending aorta 106 to be retrieved and secured outside the aorta 106 via various endoscopic techniques. The anchor member can be located adjacent at least one longitudinal end, or adjacent both longitudinal ends to tether the pump in the desired location within the descending aorta. If desired, a plurality of anchor members, such as needles, sheathed or unsheathed, with integral sutures can be located at various locations along the longitudinal length of the pump. By way of example and not limitation, the anchor members 38, such as needles with integral sutures, can be positioned at each longitudinal end of each inflatable chamber defining the pump, if desired.

Figure 9:
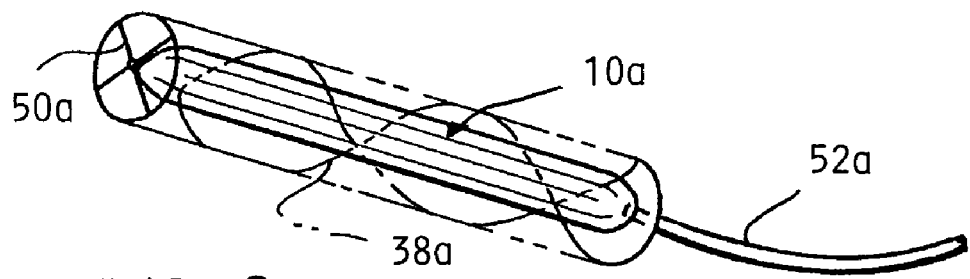
FIG. 9 is a simplified perspective view of an aortic blood pump formed as a deflated balloon pump suspended within at least one anchor member including a contracted stent prior to surgical location within an aorta of a patient.
Figure 10:
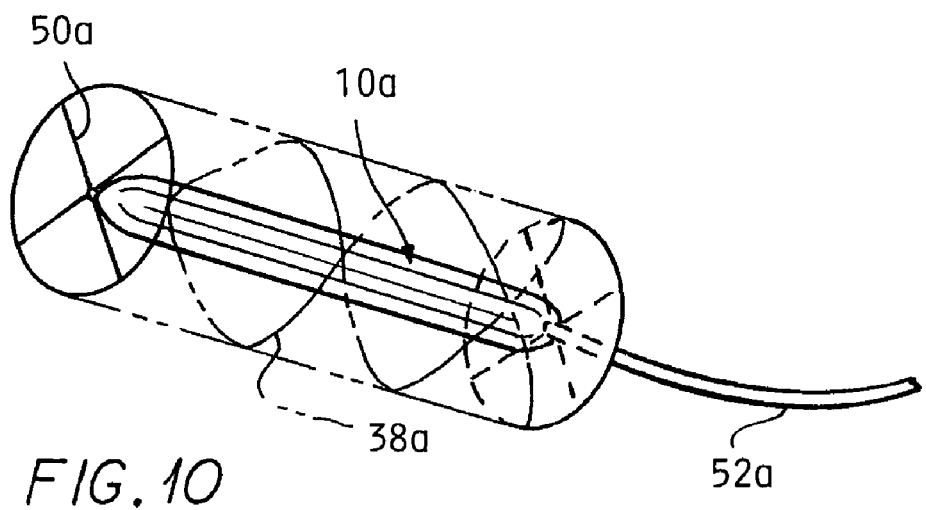
FIG. 10 is a simplified perspective view of the blood pump of FIG. 9 with the stent expanded and the balloon pump in a deflated state.
Figure 11:
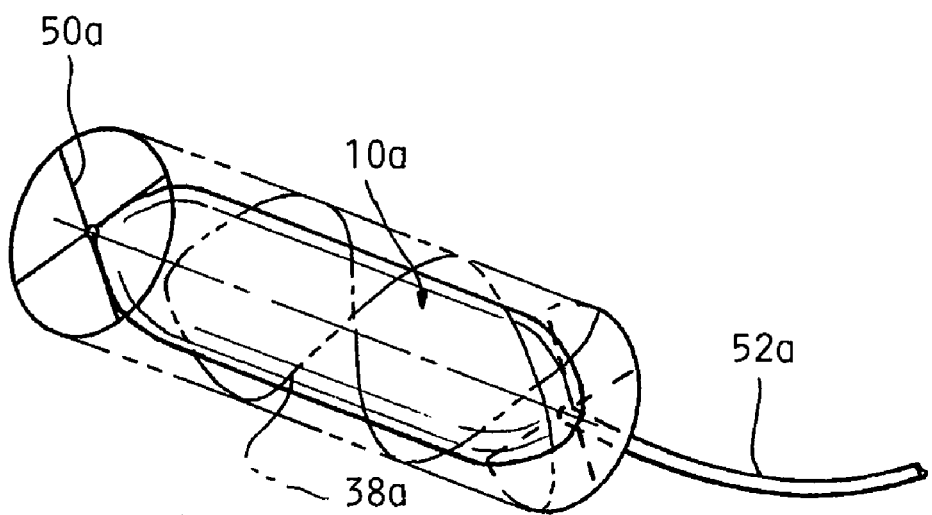
FIG. 11 is a simplified perspective view of the blood pump of FIG. 9 with the stent expanded and the balloon pump in an inflated state.

Referring now to FIGS. 9-11, a simplified perspective view of an aortic blood pump 10 formed as a balloon pump suspended within a central portion of a stent 38a is shown. The stent 38a is in a contracted or collapsed position as illustrated in FIG. 9 with the balloon pump 10a in a deflated state. The retracted position of the stent 38a and the deflated state of the balloon pump 10a allow the minimally invasive surgical positioning of the stent with respect to the aorta of a patient using any know surgical technique selected from a known variety of incision locations on the patient. The implantation is performed with a minimally invasive surgical procedure or technique. After the stent 38a has been properly positioned at the desired location within the aorta of the patient, the stent 38a is expanded to engage the inner wall of the aorta (not shown) as illustrated in FIG. 10. As can best be seen in FIG. 10, the balloon pump 10a, while still in a deflated state, remains suspended in the expanded central portion of the stent by any suitable connectors 50a or attachment known to those skilled in the art, such as the art of stent design and operation. The balloon pump 10a can then be cyclically inflated, as shown in FIG. 11, and deflated, as shown in FIG. 10, through flexible tube 52a synchronously with the heart beat of the patient to assist cardiac function in response to measured clinical parameters of the patient as described in detail in the above listed patents incorporated by reference in their entirety herein.

Figure 12:
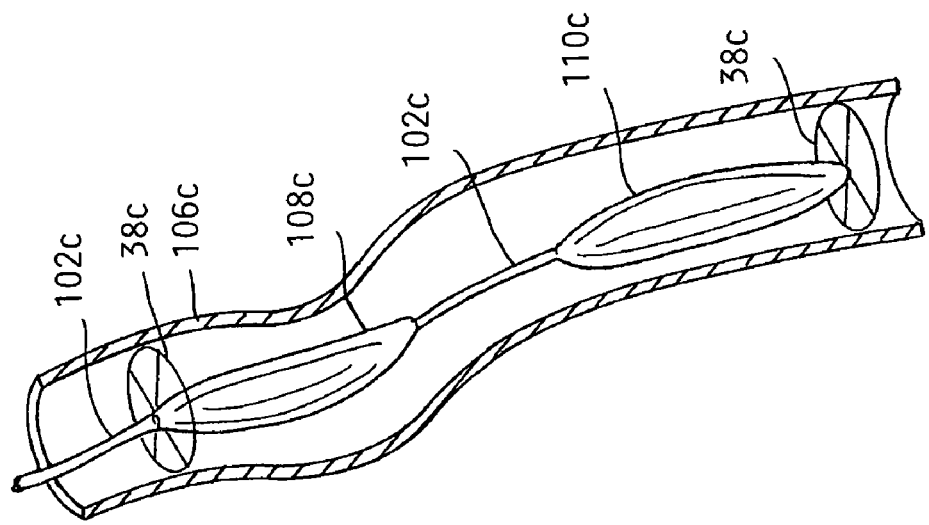
FIG. 12 is a cross-sectional view of a vascular entry into the descending aorta illustrating a double chamber, large volume, long term intra-aorta balloon pump according to the present invention in a deflated state after insertion through an upper body skin entry point and/or an upper body vascular entry point as illustrated in FIG. 2A and including at least one anchor member adjacent a longitudinal end of the pump, and preferably adjacent each longitudinal end of the pump defined by the dual inflatable chambers.

Referring now to FIG. 12, the chronic ambulatory balloon pump 108c according to the present invention can be advantageously tethered to lie on the local center line of the local segment of the aorta 106c at one or both longitudinal ends of the pump 108c, and/or at each connecting tube 102c extending between inflatable chamber segments of the pump. By way of example and not limitation, the anchor member 38c can include a short longitudinally extending segment of expandable stent-type cage secured to the pneumatic power conduit 102c connecting each inflatable chamber of the pump 108c, and/or secured to the pneumatic power conduit 102c proximal to the first inflatable chamber of the pump 108c, and/or to the tip of the catheter extending beyond the distal inflatable chamber of the pump 108c, so that after deployment of the expandable stent-type cage, the pneumatic power conduit 102c is suspended and maintained in the local center line of the aorta 106c. In the configuration, as illustrated in FIG. 12, the anchor member can include a short longitudinal lengths of expandable stent-type cage located at one or more of the longitudinal ends of the one or more inflatable chambers defining the pump 108c, where multiple chambers can be separated by longitudinal lengths of flexible conduit 102c.

Figure 13:
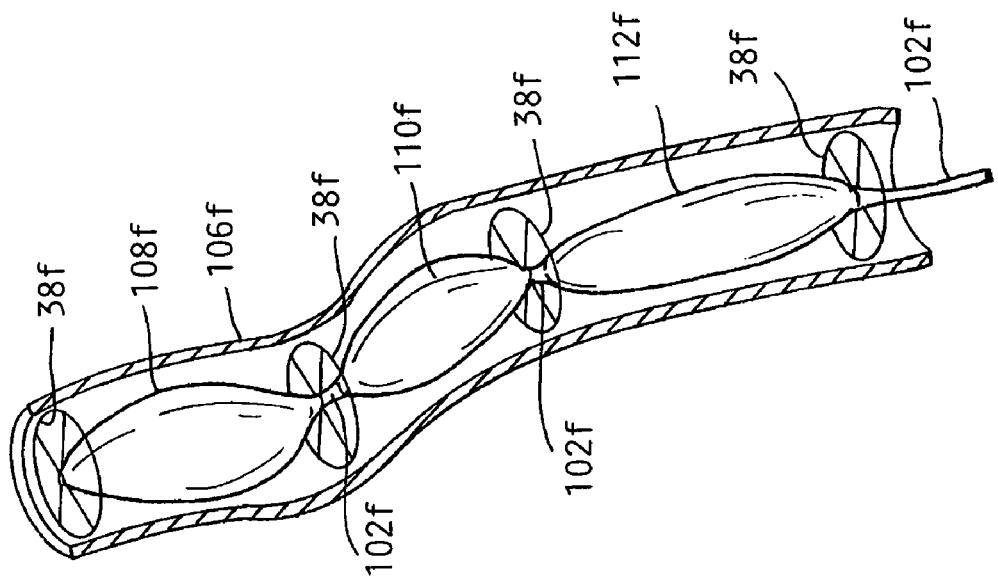
FIG. 13 is a cross-sectional view of a triple chamber balloon pump similar to FIG. 3C in an inflated state after insertion through a lower body skin entry point and/or lower body vascular entry point including at least one anchor member, and preferably a plurality of anchor members located, adjacent to at least one, and preferably each, longitudinal end of an inflatable chamber defining the pump.

Referring now to FIG. 13, the at least one anchor member 38f can be located at each longitudinal end of each inflatable chamber defining the pump 108f. In the illustrated configuration, the anchor member can include a longitudinally short section of expandable stent-type cages located at one or more longitudinal ends of the inflatable chambers defining the pump 108f and located adjacent to the flexible conduit 102f extending between adjacent inflatable chambers. In addition, longitudinally short lengths of expandable stent-type cages can be located at the distal end and the proximal end of the pump 108f within the descending aorta. Each anchor member 38f can be secured to the pneumatic power conduit 102f connecting each inflatable chamber, or to the pneumatic power conduit 102f proximal to the first inflatable chamber, or to the tip of the catheter beyond the distal inflatable chamber, so that after deployment of the anchoring member 38f, the pneumatic power conduit 102f is suspended and maintained in the local center line of the aorta 106f.

Figure 14:
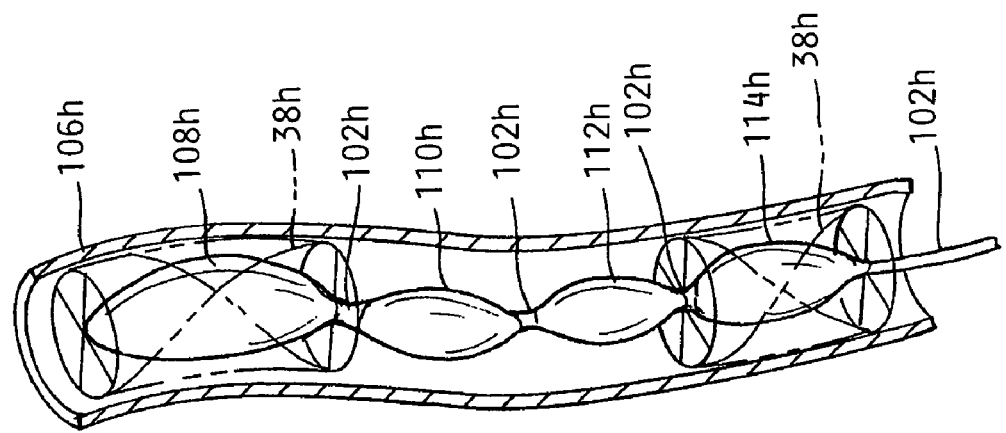
FIG. 14 is a cross-sectional view of a quadruple chamber balloon pump similar to FIG. 4C in an inflated state after insertion through a lower body skin entry point and/or lower body vascular entry point including at least one anchor member, and preferably a plurality of anchor members, according to the present invention, where a stent-type cage sheathes at least one inflatable chamber defining the pump, and preferably two inflatable chambers at opposite ends of the pump or most preferably each of the inflatable chambers defining the pump.

Referring now to FIG. 14, the chronic ambulatory balloon pump 108h according to the present invention can be advantageously tethered to lie on the local center line of the local segment of the aorta 106h at one end, or both ends, or at various locations along a longitudinal length of the connecting tube 102f between inflatable chamber segments, or any combination thereof. In the illustrated configuration, by way of example and not limitation, the at least one anchor member 38h can be a longitudinally extending stent-type cage sheathing at least one inflatable chamber defining the pump 108h. Preferably, the sheathing cages are secured at opposite ends of each inflatable chamber and are expandable into contact with an inner wall of the descending aorta 106h in order to tether the pump 108h in a desired location at one longitudinal end, or at both longitudinal ends, or along one or more of the inflatable chambers defining the inflatable multi-chamber pump 108h.

Figure 15:
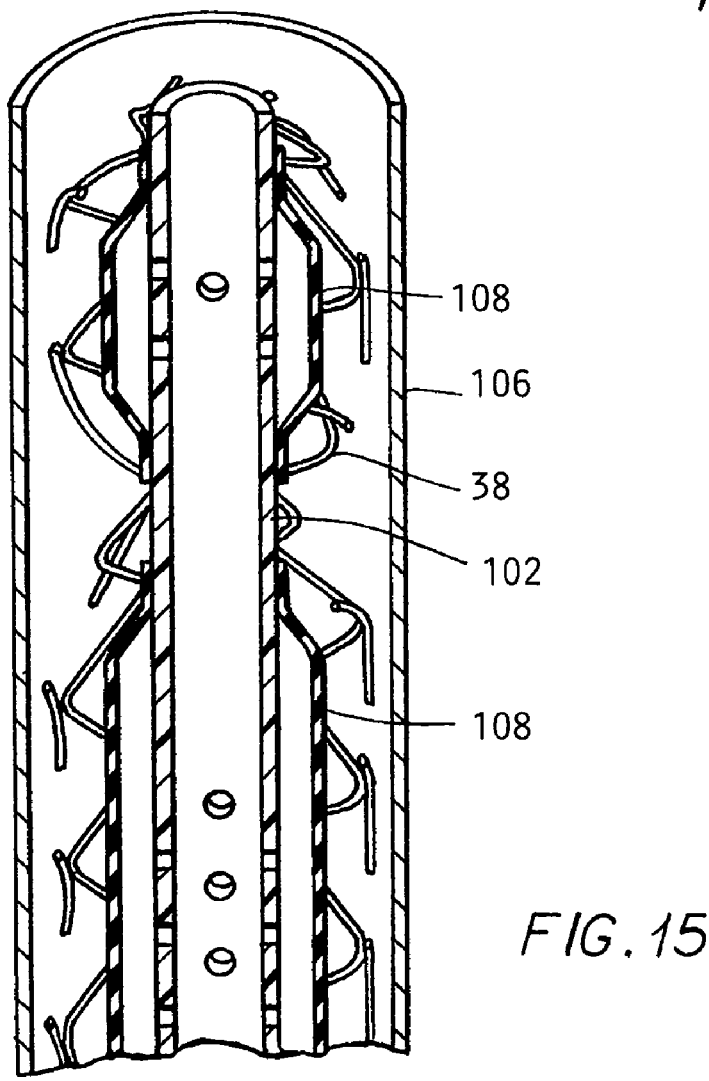
FIG. 15 is a detailed cross-sectional view of a multi-chamber balloon pump in an inflated state with at least one anchor member, such as stent-type cage, sheathing each inflatable chamber defining the pump.

In the preferred configuration, the at least one anchor member 38 can include an expandable stent-type cage sheathingly engaging each of the inflatable chambers defining the pump 108 for positioning within a descending aorta 106 of a patient, as illustrated in the exploded detail of FIG. 15. As best seen in FIG. 15, the sheathing cages can taper inwardly toward the flexible conduit 102 extending between adjacent inflatable chambers of the pump 108. In addition, the inflatable chambers can be of different size volumes independent of one another. Each chamber is inflatable through passages communicating from the flexible conduit 102 and in communication with the interior of the inflatable chamber defined by the flexible membrane. The sheathing cage or mesh tube can taper down to meet the power conduit 102 between each chamber of a multi-chamber pump 108.

The illustrated configurations described according to the present invention can provide the ability to custom design modular assemblies of multiple inflatable chambers as determined by a step-wise linear approximation of a particular individual patient's aorta 106. The mesh tube can be discontinuous between each pumping chamber, i.e. there can be a separate mesh tube associated with each pumping chamber.

Also, the inflatable chamber modules can be manufactured in a variety of lengths and diameters. The chronic ambulatory balloon pump 108 according to the present invention can be advantageously custom fitted to an individual patient. By way of example and not limitation, prior to implantation, images of a patient's thoracic and abdominal aorta can be obtained by medical imaging means. The medical imaging means, by way of example and not limitation, can include CT scanning, MRI scanning, ultrasound imaging, and multi-planar aortography. The image data can then be reviewed, for example via a computer, details of the curvature, inner diameter, branching pattern, and other anatomic information can be noted. The anatomic information can then be used to select an appropriately-sized long term ambulatory balloon pump configuration. Appropriate sizing of the long term ambulatory balloon pump configuration can involve selection of the length, diameter and displacement of each of the pumping chambers, as well as optionally, length, and diameter of each of these segments of expandable stent-type cage or mesh tube described in greater detail above. A range of sizes can be provided by a manufacturer for several complementary manufacturing processes according to the present invention. A stock process can provide a commonly needed configuration manufactured prior to identification of an individual patient. In this process, the aortic imaging data is simply used to select an existing inflatable chamber configuration of a pump 108 appropriate for the individual patient. A semi-custom process according to the present invention can also be used. In this process, the aortic imaging data can be used to select a series of individual, pre-manufactured inflation chamber modules which are then assembled length wise into a completed pump 108 appropriate to the aortic anatomy of an individual patient. Methods of assembling individual inflatable chamber module segments into a completed pump 108 can include, by way of example and not limitation, individual inflatable chambers being slid onto a common catheter 102 and then sealed in an airtight fashion; or individual inflatable chamber modules, each with its own segment of pneumatic power conduit 102 can be connected in series to form the multi chamber balloon pump 108. A custom process according to the present invention can also be used. In this process, the aortic imaging data can be used to design or manufacture a series of individual inflatable chamber modules which can then be assembled lengthwise into a completed pump 108 appropriate to the aortic anatomy of an individual patient. Methods of assembling individual inflatable chamber module segments of the pump 108 into a completed device can include, by way of example but not limitation, individual pumping modules can be slid onto a common catheter 102 and then sealed in an airtight fashion; or individual pumping chamber modules come each with its own segment of pneumatic conduit 102 can be connected in series to form the completed multi-chamber balloon pump 108. It should be recognized that a combination of the processes according to the present invention as described above can be used while being mutually compatible for combination with one another in order to optimize clinical and manufacturing efficiencies.

It should also be recognized that the balloon pump 108 according to the present invention advantageously can be manufactured with a textured surface, such as that used in the manufacture of the blood pumping membrane of the Kantrowitz CARDIOVAD® device described in the patents incorporated by reference above. It is believed that cell formation and growth may encourage adhesion of a fibrin platelet matrix for the pumping chamber can allow subsequent neo-intimization process as described in the L.VAD patents incorporated by reference herein.

Figure 16:
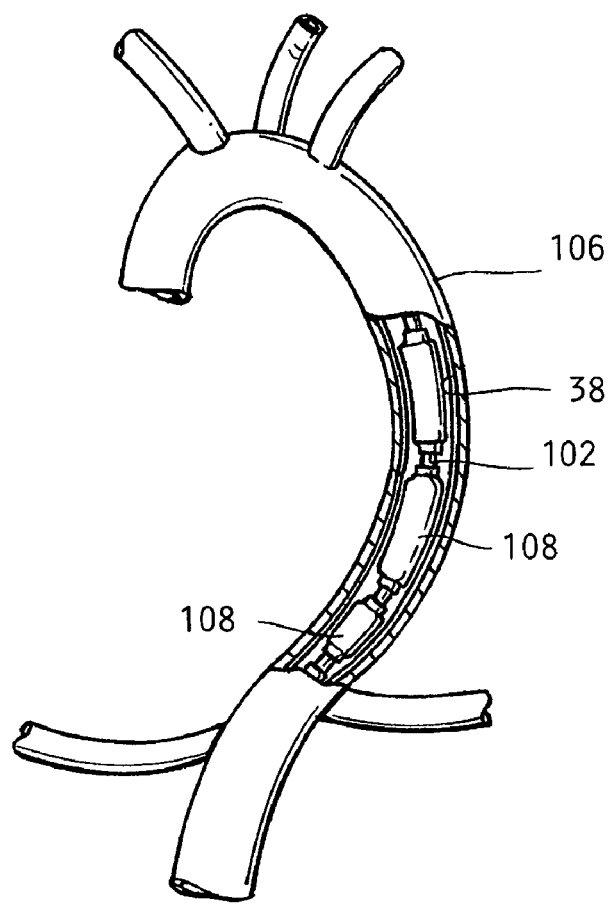
FIG. 16 is a partial cross-sectional front elevational view of a balloon pump according to the present invention positioned within the descending aorta while depicting a three-dimensional serpentine tortuous descending aorta.
Figure 17:
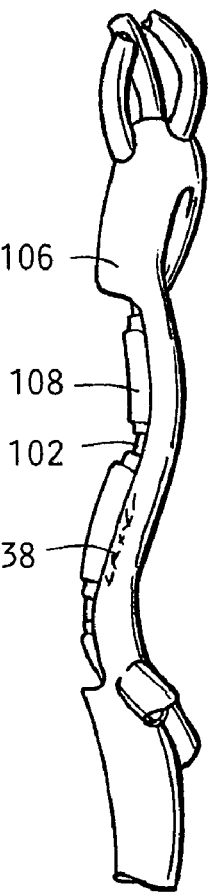
FIG. 17 is a partial cross-sectional side elevational view of the three-dimensional serpentine tortuous descending aorta depicted in FIG. 16.

Referring now to FIGS. 16 and 17, a chronic ambulatory multi-chamber balloon pump 108 according to the present invention is illustrated positioned within a descending aorta 106 of a patient. The intra luminal balloon pump 108 can have at least one elongate inflatable chamber positionable to be lying completely within a descending aorta 106 of the patient. At least one anchor member 38 is provided for anchoring the balloon pump 108 in a location within the descending aorta 106. The anchor member 38 can include one or more anchor members 38 located in at least one position selected from a distal end of the balloon pump 108, a proximal end of the balloon pump 108, an intermediate segment of flexible conduit 102 between adjacent inflatable chambers, sheathing at least a portion of at least one inflatable chamber, or sheathing an entire longitudinal length of the multi inflatable chamber balloon pump 108. The balloon pump 108 according to the present invention can include tapered longitudinal ends and/or be segmented into a plurality of pumping chamber sub-segments, each pumping chamber sub-segment separated by a flexible power conduit 102 length, where the diameter of the pumping chamber sub-segments are independent of one another.

Figure 18:
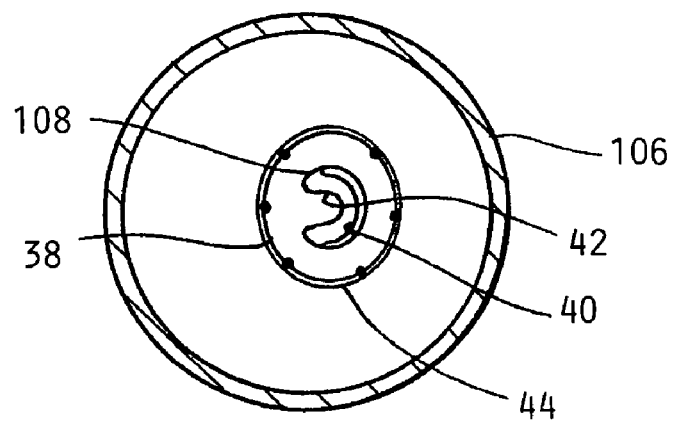
FIG. 18 is a simplified schematic cross-sectional view of a semi-rigid shell portion and a relatively thin flexible membrane portion defining an inflatable chamber of a pump in a deflated state surrounded by a retracted stent-type cage during insertion into a descending aorta of a patient.
Figure 19:
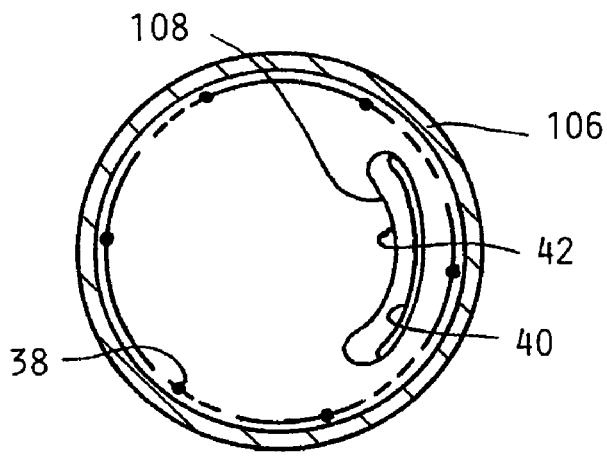
FIG. 19 is a simplified schematic cross-sectional view of the inflatable chamber illustrated in FIG. 18 with the semi-rigid shell portion and the relatively thin flexible membrane portion defining the inflatable chamber and with the stent type cage in an expanded position to anchor the semi-rigid shell portion against the inner side wall of the aorta in an eccentric location with respect to the center line of the local aorta.
Figure 20:
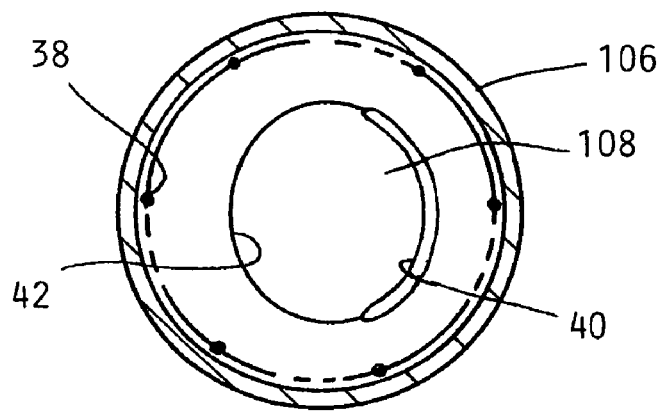
FIG. 20 is a simplified schematic cross-sectional view of the inflatable chamber illustrated in FIGS. 18 and 19 with the inflatable chamber of the pump in an inflated state according to the present invention.

Referring now to FIGS. 18 through 20, a chronic ambulatory balloon pump 108 according to the present invention is illustrated. The inflatable balloon pump 108 can be anchored with respect to the wall of the aorta 106 for minimally invasive surgical positioning with respect to the aorta 106 of the patient. After engagement of the anchor member 38 in a selected location of the aorta 106, the inflated balloon pump 108 can be cyclically inflated and deflated to assist the cardiac function based on measured clinical parameters of the patient. At least one anchor member 38 can be provided for tethering the pump 108 with respect to the desired location in the aorta 106. The anchor member 38 can be located adjacent at least one longitudinal end of the pump 108, or each longitudinal end of each inflatable chamber defining the pump 108, or sheathing at least one of the inflatable chambers defining the pump 108. In the illustrated configuration of FIG. 18, the intra-luminal balloon pump 108 can include a semi-rigid surface or admural portion 40 facing an internal wall of the descending aorta 106, and a flexible pumping membrane, adluminal portion 42 facing an opposite aortic lumin. The inflatable chamber illustrated in FIG. 18 is in a retracted position and is surrounded by a retracted anchor member 38 defined by an expandable stent-type cage 38, and an optional removable sheath 44 can be provided to maintain the retracted position of the wire stent during implantation. In the event the clinician elects to remove the long term intra-aortic balloon pump, a sheath 44 can be re-introduced to sequentially collapse each of the wire meshes and corresponding pumping chambers. Note, that the porosity of the wire mesh of the expanded stent allows for largely unimpeded flow into branch vessels leaving the aorta in the vicinity of the pumping chamber.

The anchor member 38 can include a non-axial-symmetric, eccentric, locating anchor for positioning the admural surface of the inflatable chamber immediately proximate to an internal wall of the aorta 106. As can best be seen in FIG. 19, when the anchor 38 is expanded, the stent-type cage engages the inner wall of the aorta 106 in order to tether the associated admural surface of the inflatable chamber in a position immediately proximate to an internal wall of the aorta 106. An optional surface treatment can be provided on the admural surface for encouraging fibrous ingrowth and sicatrixization of the admural surface 40 of the pumping chamber to the inner wall of the aorta. Subsequent to this process, it is expected that neo-intimization can then proceed from the periphery of the admural surface to cover the adluminal surface 42, as is true for the CARDIOVAD® device. As best seen in FIG. 20, the inflatable chamber of the pump 108 can be expandable from the deflated state illustrated in FIG. 19 to the inflated state illustrated in FIG. 20 in order to provide cardiac assistance to the patient. In this configuration, the anchor member 38 can include at least one expandable stent-type cage secured to the balloon pump 108, such that after deployment of the expandable stent-type cage, the balloon pump 108 can be suspended and maintained in an asymmetric location with respect to a local center line of the aorta 106 of the patient. The non-axial-symmetric multi-chamber long term ambulatory intra-aortic balloon pump 108 according to the present invention can be positioned using minimally invasive surgical procedures in order to position the pump 108 in a selected location of the aorta 106. The multi-chamber long term ambulatory intra-aortic balloon pump 108 can be preferably located in an eccentric location of the aorta 106 immediately proximate to the internal aortic wall. In order to achieve the eccentric location, the non-axial-symmetric multi-chamber long term ambulatory intra-aortic balloon pump 108 can be provided with a non-axial-symmetric pumping chamber including a semi-rigid admural surface 40 facing a selected aortic wall, and a flexible pumping adluminal membrane 42 facing the remaining aortic lumin. The surfaces can be similar to those described in the Kantrowitz CARDIOVAD® configuration described in the patents incorporated by reference above, even though the present device is intended to be positioned within the lumin of the aorta 106 rather than being integrated into the wall structure of the aorta 106 as is described in those patents incorporated by reference. The expandable stent-type cage of the axial-symmetric multi-chamber long term ambulatory intra-aorta balloon pump 108 are configured to position the power conduit 102 away from the center line of the local aorta 106 to a position proximate to the inner aortic wall. In an alternative embodiment, the stent cage 38 can be secured to the admural surface 40, or partially embedded therein, and is not tapered toward the power conduit 102, but rather is a simple tubular shape with open ends. The specific advantage of this alternative embodiment is that it removes the tapered ends of the neck cages (illustrated in FIG. 15), thereby allowing for less impediment to aortic blood flow. The expanding stent-type cages can be longitudinally extended and secured to the semi-rigid admural surface of the pumping chamber and can serve to keep the semi-rigid admural surface 40 intimately apposed to the inner aortic wall. This apposition will allow migration of vascular endothelial cells onto the adluminal surface of the pumping chamber, thereby encouraging neo-intima formation as described for the Kantrowitz CARDIOVAD® device described in the patents incorporated by reference above.

In order to accommodate tortuosity of the aorta 106 in individual patients, the process of modular assembly of several pumping chambers into a single pump 108 implant can be used for the non-axial-symmetric multi-chamber long-term ambulatory intra-aortic balloon pump 108 as described in greater detail above.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A long-term ambulatory intra-aortic balloon pump system for providing left ventricular cardiac assistance to a patient comprising:
    an external drive system for supplying a compressed fluid, the drive system operating in accordance with a control program stored in memory;
    an intra-luminal balloon pump having an elongate inflatable chamber positionable to be lying completely within a descending aorta of the patient; and
    a percutaneous access device for connecting in fluid communication the intra-luminal balloon pump with the compressed fluid to be supplied by the external drive system, wherein the elongate inflatable chamber is inflated and deflated synchronously with a heartbeat of the patient in accordance with the control program stored in memory of the external drive system, wherein the percutaneous access device is a biocompatible implantable portal comprising a communicative passage through an interior bore and an exterior having a neck region adapted to promote autologous cell growth thereon in an implantable region, the neck region having a plurality of channels extending about the neck region.

2. The system of claim 1, wherein the elongate inflatable chamber is elongated along a longitudinal axis when inflated so there is no increase in aorta cross section.

3. The system of claim 1, wherein the external drive system supplies compressed air to the percutaneous access device through a large diameter conduit.

4. The system of claim 1, wherein the percutaneous access device comprises cultured cells.

5. The system of claim 1, wherein each channel has a width of 20 to 300 microns.

6. The system of claim 1, wherein adjacent channels are separated by a plateau having a width of between 0 and 600 microns.

7. The system of claim 1, wherein the exterior is nanotextured.

8. The system of claim 1 further comprising an autologous cell growth promoter coating.

9. The system of claim 1, wherein the external drive system supplies compressed air to the percutaneous access device through a large diameter conduit.

10. The system of claim 9, wherein the elongate inflatable chamber has an inflated volume of between 50 cc to 65 cc, inclusive.

11. A long-term ambulatory intra-aortic balloon pump system for providing left ventricular cardiac assistance to a patient comprising:
    an external drive system for supplying a compressed fluid, the drive system operating in accordance with a control program stored in memory;
    an intra-luminal balloon pump having an elongate inflatable chamber positionable to be lying in a descending aorta completely downstream of the aortic arch and carotid arteries of the patient; and
    a percutaneous access device for connecting in fluid communication the intra-luminal balloon pump with the compressed fluid to be supplied by the external drive system, the device comprising a wall defining a bore and an exterior having a neck region adapted to promote autologous cell growth thereon in an implantable region, and
    wherein the elongate inflatable chamber is inflated and deflated synchronously with a heartbeat of the patient in accordance with the control program stored in memory of the external drive system.

12. The system of claim 11, wherein the bore defined by the wall is sufficiently sized to supply compressed air from the external drive system through a large diameter conduit.

13. The system of claim 12, wherein the elongate inflatable chamber is elongated along a longitudinal axis when inflated so there is no increase in aorta cross section.

14. The system of claim 11, wherein the neck region has a plurality of channels extending about the neck region.

15. The system of claim 14, wherein the percutaneous access device further comprises a manifold encompassing the neck region so as to form a seal therebetween and a route of fluid communication between a manifold inlet and at least one of the plurality of channels.

16. The system of claim 15 further comprising a gasket in simultaneous contact between the manifold and the neck region.

17. The system of claim 14, wherein each channel has a width of 20 to 300 microns and are separated by a plateau having a width of between 0 and 600 microns.

18. The system of claim 11, wherein the elongate inflatable chamber has an inflated volume of between 50 cc to 65 cc, inclusive.

19. The system of claim 11, wherein the neck region comprises an autologous cell growth promoter coating.

20. A long-term ambulatory intra-aortic balloon pump system for providing left ventricular cardiac assistance to a patient comprising:
an external drive system for supplying a compressed fluid, the drive system operating in accordance with a control program stored in memory;
an intra-luminal balloon pump having an elongate inflatable chamber positionable to be lying in a descending aorta completely downstream of the aortic arch and carotid arteries of the patient; and
a percutaneous access device for connecting in fluid communication the intra-luminal balloon pump with the compressed fluid to be supplied by the external drive system, the device comprising a wall defining a bore and an exterior having a neck region adapted to promote autologous cell growth thereon in an implantable region, and with a pore size and configuration which avoids regions which are of a geometry to allow bacteria to grow and multiply but which are of the pore size and configuration which would interfere with a body's white cells from reaching the bacteria.

21. The system of claim 20, wherein the bore defined by the wall is sufficiently sized to supply compressed air from the external drive system through a large diameter conduit.

22. The system of claim 21, wherein the elongate inflatable chamber is elongated along a longitudinal axis when inflated so there is no increase in aorta cross section.

23. The system of claim 20, wherein the neck region has a plurality of channels extending about the neck region.

24. The system of claim 23, wherein the percutaneous access device further comprises a manifold encompassing the neck region so as to form a seal therebetween and a route of fluid communication between a manifold inlet and at least one of the plurality of channels.

25. The system of claim 23, wherein each channel has a width of 20 to 300 microns and are separated by a plateau having a width of between 0 and 600 microns.

26. The system of claim 20, wherein the elongate inflatable chamber has an inflated volume of between 50 cc to 65 cc, inclusive.

27. The system of claim 20, wherein the neck region comprises an autologous cell growth promoter coating with the appropriate pore size and configuration.

* * * * *